(12) United States Patent
Koops (10) Patent No.: US 7,127,759 B2
(45) Date of Patent: Oct. 31, 2006

(54) PILLOW FOR PREVENTING SNORING

(75) Inventor: Jan Koops, Groningen (NL)

(73) Assignee: KK&B Connection Holding B.V., Groningen (NL)

( * ) Notice: Subject to any disclaimer, the term of this patent is extended or adjusted under 35 U.S.C. 154(b) by 0 days.

(21) Appl. No.: 10/506,587

(22) PCT Filed: Jan. 10, 2003

(86) PCT No.: PCT/NL03/00014

§ 371 (c)(1), (2), (4) Date: Apr. 26, 2005

(87) PCT Pub. No.: WO03/079943

PCT Pub. Date: Oct. 2, 2003

(65) Prior Publication Data

US 2005/0172409 A1     Aug. 11, 2005

(30) Foreign Application Priority Data

Mar. 4, 2002  (NL) .................................. 1020108
Apr. 26, 2002 (NL) .................................. 1020477
Dec. 30, 2002 (NL) .................................. 1022279

(51) Int. Cl.
A47G 9/10 (2006.01)

(52) U.S. Cl. .................................. 5/644; 5/640; 5/636

(58) Field of Classification Search .................. 5/644, 5/645, 640, 636, 490, 654, 655.3, 655.9, 5/953

See application file for complete search history.

(56) References Cited

U.S. PATENT DOCUMENTS

| | | | | |
|---|---|---|---|---|
| 2,822,554 A | * | 2/1958 | Wenzelberger | 5/644 |
| 3,242,511 A | * | 3/1966 | Fultz et al. | 5/655.9 |
| 3,243,828 A | * | 4/1966 | McCarty | 5/636 |
| 4,193,150 A | * | 3/1980 | Vineberg | 5/632 |
| 4,320,543 A | * | 3/1982 | Dixon | 5/637 |
| 4,501,034 A | * | 2/1985 | Greenawalt | 5/644 |
| 4,756,035 A | * | 7/1988 | Beier | 5/640 |
| 4,780,921 A | * | 11/1988 | Lahn et al. | 5/630 |
| 4,803,743 A | * | 2/1989 | Greenawalt | 5/636 |
| 4,807,313 A | * | 2/1989 | Ryder et al. | 5/610 |
| 4,829,614 A | * | 5/1989 | Harper | 5/644 |
| 4,918,774 A | * | 4/1990 | Popitz | 5/644 |
| 4,947,500 A | * | 8/1990 | Seiler | 5/713 |
| 5,016,303 A | * | 5/1991 | Tanaka et al. | 5/636 |
| 5,068,933 A | * | 12/1991 | Sexton | 5/644 |
| 5,137,333 A | * | 8/1992 | Chee | 297/452.21 |
| 5,231,720 A | * | 8/1993 | Benoff | 5/644 |
| 5,528,784 A | * | 6/1996 | Painter | 5/640 |
| 5,638,564 A | * | 6/1997 | Greenawalt et al. | 5/636 |
| 5,642,543 A | | 7/1997 | Huntley | |
| 5,682,633 A | * | 11/1997 | Davis | 5/636 |
| 5,771,514 A | * | 6/1998 | Wilhoit | 5/644 |

(Continued)

FOREIGN PATENT DOCUMENTS

CH     609 850 A5     3/1979

(Continued)

*Primary Examiner*—Robert G. Santos
(74) *Attorney, Agent, or Firm*—Kinney & Lange, PA (57) ABSTRACT

The invention relates to a pillow system for preventing snoring. For that purpose, the pillow system is provided with an adjustable pillow (2) that is placed on top of a basis element (1) made of a high-density foam product. On top, a flap (3) made of a low-density foam product or a traditional pillow is placed. Round these constituent parts (1, 2, 3), a cover (7), made for an elastic material is placed.

13 Claims, 6 Drawing Sheets

U.S. PATENT DOCUMENTS

| | | | |
|---|---|---|---|
| 5,771,515 A * | 6/1998 | Carr | 5/660 |
| 5,781,947 A * | 7/1998 | Sramek | 5/636 |
| 5,926,879 A * | 7/1999 | Davis | 5/636 |
| 5,953,777 A * | 9/1999 | Buck | 5/636 |
| 5,987,675 A * | 11/1999 | Kim | 5/636 |
| 6,006,380 A * | 12/1999 | Sramek | 5/636 |
| 6,047,425 A * | 4/2000 | Khazaal | 5/644 |
| 6,124,578 A | 9/2000 | Elliot | |
| 6,131,219 A * | 10/2000 | Roberts | 5/644 |
| 6,182,312 B1 * | 2/2001 | Walpin | 5/636 |
| 6,317,908 B1 * | 11/2001 | Walpin | 5/636 |
| 6,327,725 B1 * | 12/2001 | Veilleux et al. | 5/644 |
| 6,408,467 B1 * | 6/2002 | Walpin | 5/636 |
| 6,446,288 B1 * | 9/2002 | Pi | 5/636 |
| 6,757,925 B1 * | 7/2004 | Toomer | 5/660 |
| 6,925,670 B1 * | 8/2005 | Torrez | 5/731 |
| 2005/0172409 A1 * | 8/2005 | Koops | 5/636 |

FOREIGN PATENT DOCUMENTS

| | | |
|---|---|---|
| DE | 195 35 232 C2 | 7/1998 |
| DE | 199 30 818 C1 | 5/2001 |
| EP | 0 513 042 B1 | 1/1994 |
| EP | 0 404 843 B1 | 12/1994 |
| FR | 2 678 815 | 1/1993 |

* cited by examiner

PILLOW FOR PREVENTING SNORING

The invention relates to a pillow system for preventing snoring. A pillow for preventing snoring is for example known from EP-A 0 404 843. With this known pillow one tries to position the head of a user such that the pharynx remains open and that consequently snoring is prevented.

With the present invention, one aims at preventing snoring by tightening the tissues of the mouth and the pharynx of the user, which has as a result that resonances in the mouth and in the pharynx cannot develop. This is achieved by forcing the head of the user, lying on a side, into such a position that the head forms a small angle with respect to a prolongation of the spinal column. The problem is that this position of the head must be determined for each individual, dependent upon his physical parameters and upon the basis on which he sleeps, because too small an angle will prevent snoring insufficiently while too large an angle will be uncomfortable for the user.

In order to have on the one side enough possibilities for adjusting the pillow and to realise on the other side a stable pillow system, the inventive pillow system is characterised in that the pillow system comprises at least a basis element made of foam rubber, polyurethane foam, polyether foam or a comparable foam product, an adjustable pillow fitted onto the basis element and a cover for enclosing the basis element and the adjustable pillow. The basis element will keep the adjustable pillow in place, while the thickness of the pillow can be adjusted dependent upon the person and the basis.

A favourable embodiment with which the adjustment of the pillow can be made in a simple manner is characterised in that the adjustable pillow is an inflatable pillow. The stability of the pillow system, once it has been adjusted, can be improved further by stabilising the position of the inflatable pillow. A further embodiment of the inventive pillow system is thereto characterised in that the basis element is provided with a depression, under operational condition transverse positioned to a user, which at least partly encloses the inflatable pillow.

A further favourable embodiment of the inventive pillow system with which the comfort for the user can be improved significantly is characterised in that on one side the basis element is provided with a flap made of foam rubber, polyurethane foam, polyether foam or a comparable foam product and that under operational conditions the flap is positioned on top of the inflatable pillow. This flap forms in fact a comfortable layer between the face of the user and the inflatable pillow. Preferably, the basis element is made of a relatively high density foam rubber, polyurethane foam, polyether foam or a comparable foam product and the flap of relatively low density foam rubber, polyurethane foam, polyether foam or a comparable foam product.

A favourable alternative embodiment of the inventive pillow system is characterised in that the basis element is at least substantially flat and that the adjustable pillow is in a longitudinal cross section at least substantially wedge-shaped. When the wedge-shape is realised with the aid of an inflatable pillow, the wedge-shape can be adjusted simply by changing the pressure in the inflatable pillow.

A further alternative embodiment is characterised in that the adjustable pillow comprises a number of layers made of a relatively high density foam rubber, polyurethane foam, polyether foam or a comparable foam product. A user is free to remove layers or to add layers again, until a height is reached which is optimal for him. Preferably, at least one layer is in a longitudinal direction wedge-shaped, so that the angle or the wedge-shape can be adjusted.

In order to increase the comfort for the user, the topside of the pillow system is preferably provided with a layer of a relatively low-density foam rubber, polyurethane foam, polyether foam or a comparable foam product. If desired, a traditional pillow may be included in the cover, together with this layer or instead of this layer, which means that a user can sleep on his familiar pillow and nevertheless enjoy the advantages of the inventive pillow system.

The stability of the pillow system can be improved further by making the cover to contribute to this stability. A favourable embodiment is thereto characterised in that the cover is made of an elastic material and can be placed around the other constituent parts of the pillow system.

The invention will now be further explained with a reference to the following figures, in which.

Figure 1A:
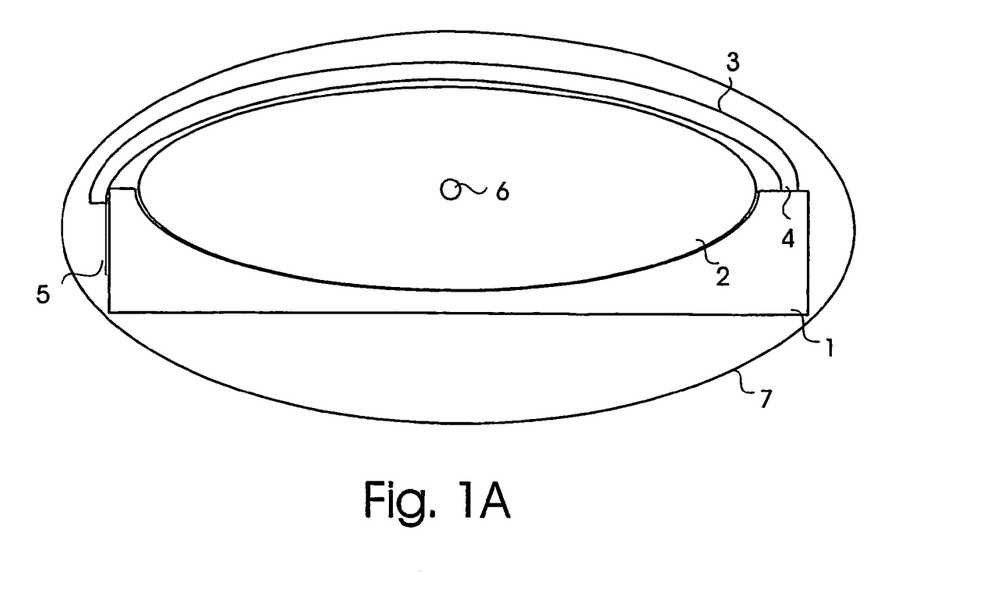
FIG. 1A represents an embodiment of the inventive pillow system in side view.

FIG. 1A represents an embodiment of the inventive pillow system in side view, consisting of a basis element 1 made of foam rubber, polyurethane foam, polyether foam or a comparable foam product with a relatively high density. In basis element 1 an inflatable pillow 2 is placed, made of for example canvas reinforced rubber or a synthetic foil, like polyurethane, that is in cross section slightly elliptically shaped and that fits well in the depression of basis element 1. In order to fasten inflatable pillow 2 even further in the depression of basis element 1, a top layer 3 is provided, one side of which is attached with for example a glued seam 4 and an opposite side of which can be stretched and fixed with for example some Velcro strips 5. An additional function of top layer 3 is increasing the comfort for a user of the pillow system. For that reason, top layer 3 is made of foam rubber, polyurethane foam, polyether foam or a comparable foam product with a relatively low density, thanks to which it feels soft. Inflatable pillow 2 is provided with a connection 6, via which air or another gas or liquid can be pressed into inflatable pillow 2 or conversely left out. Finally, a cover 7 is pulled over the pillow system which is made of an elastic fabric, for example of so called stretch textile, which cover 7 is shown in the figure in a strained situation but which will under operational conditions tightly enclose the other components of the pillow system and prevent in this way the components from moving with respect to one another. The pillow system thus obtained can subsequently be slipped into an ordinary pillowcase.

Figure 1B:
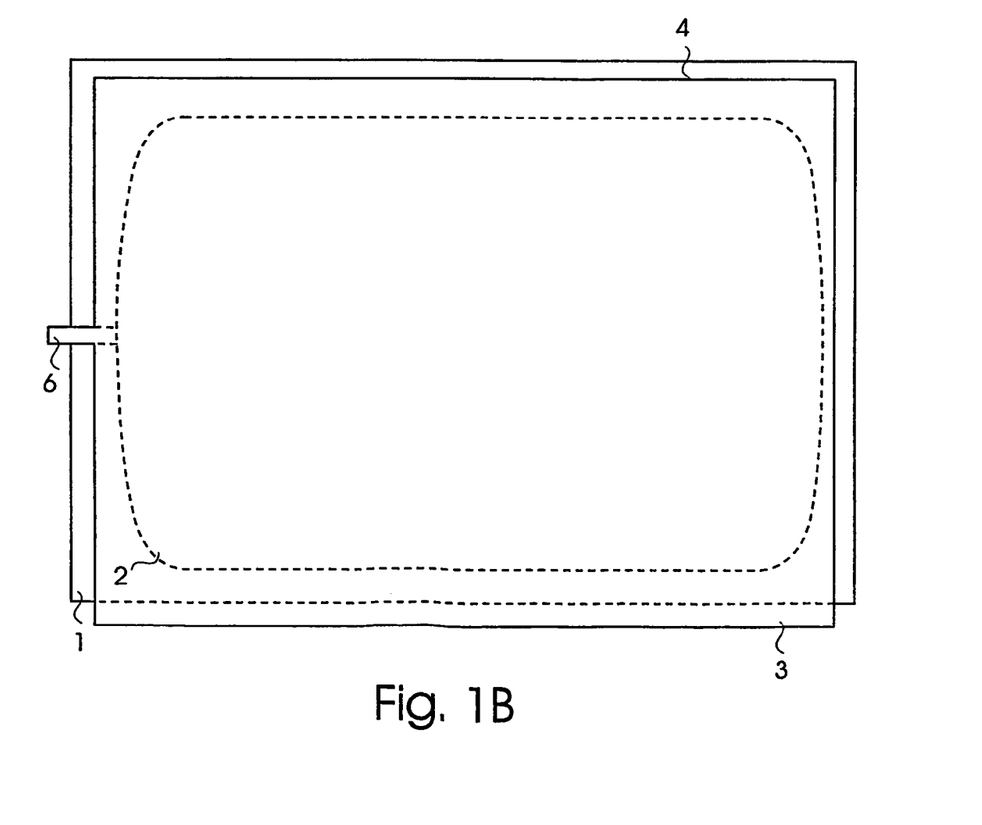
FIG. 1B represents this embodiment of the pillow system in top view.

FIG. 1B represents this embodiment of the pillow system in top view, where on top of a basis element 1 an inflatable pillow 2 is placed which is kept in place by a top layer 3, which is on one side connected with for example a glued seam 4 and of which an opposite side can be stretched and fixed. Moreover, a connection 6 of inflatable pillow 2 is visible, which can be connected to an air supply or can be used for inflating the pillow by breathing into it.

Figure 2A:
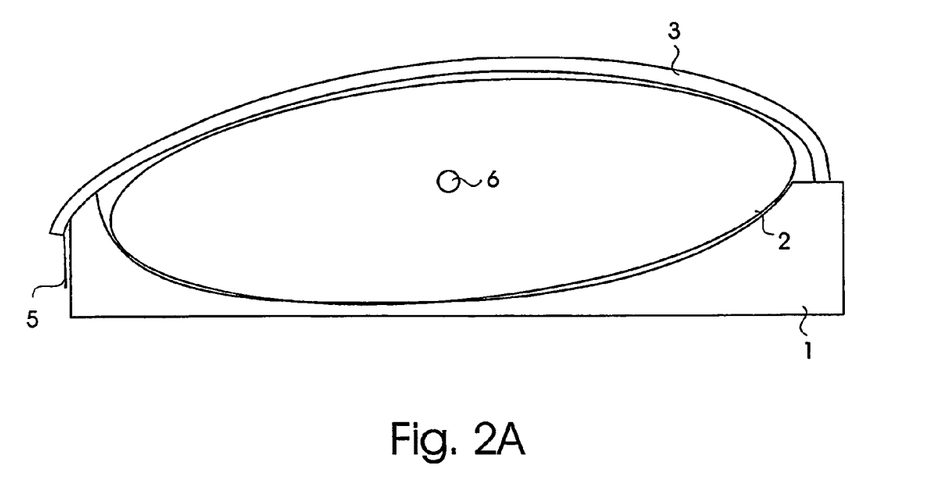
FIG. 2A represents the pillow system in a first possible position.
Figure 2B:
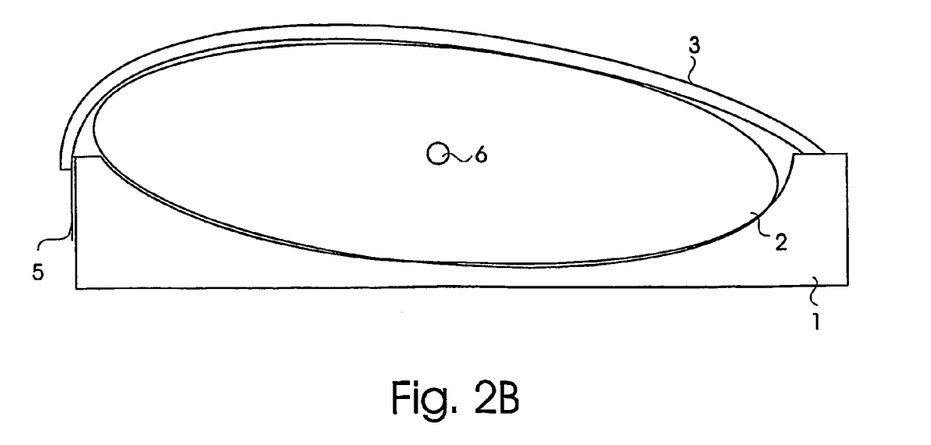
FIG. 2B represents the pillow system in a second possible position.

FIG. 2A represents the pillow system in a first possible position and FIG. 2B represents the pillow system in a second possible position, which immediately makes clear that any possible position between them can be reached simply by releasing fastening 5, turning back top layer 3, slightly moving inflatable pillow 2 and subsequently fitting top layer 3 and fixing fastening 5. Also more extreme positions than the ones shown here are possible, resulting in a continuous range of supporting positions for the head. According to the invention, a support position must be found in which the mouth—and/or the pharynx tissues are stretched, to such an extent that the user suffers little discomfort and that at the same time snoring is withheld.

Figure 3A:
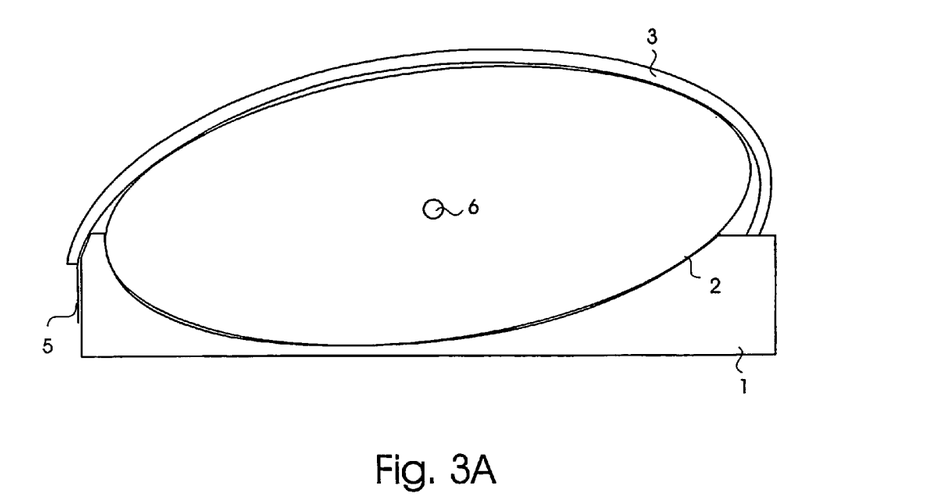
FIG. 3A represents a more inflated pillow system in a first possible position.
Figure 3B:
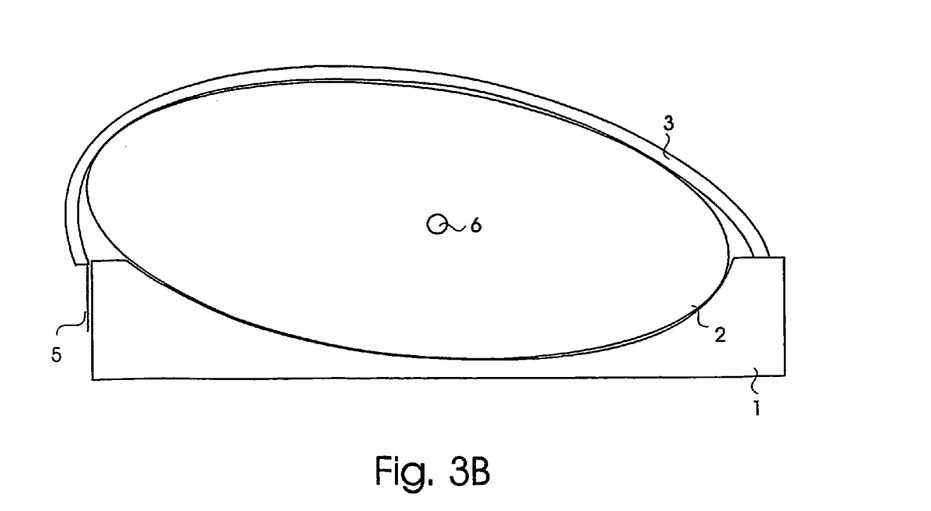
FIG. 3B represents a more inflated pillow system in a second possible position.

FIG. 3A represents a more inflated pillow system in a first possible position and FIG. 3B represents a more inflated pillow system in a second possible position. These positions can be reached by further inflating inflatable pillow 2, without the need to remove top layer 3. By selecting a material for top layer 3, one must keep in mind that it must be sufficiently stretchy to follow the pillow when it is inflated. Through that, it becomes possible to optimise first the position of inflatable pillow 2 and subsequently to inflate the inflatable pillow so far that the user suffers little discomfort and can fall asleep. In case the user of the pillow system would start snoring again, then the snorer himself or for example a roommate may further inflate the pillow, for example with bellows, until the snoring stops.

Figure 4A:
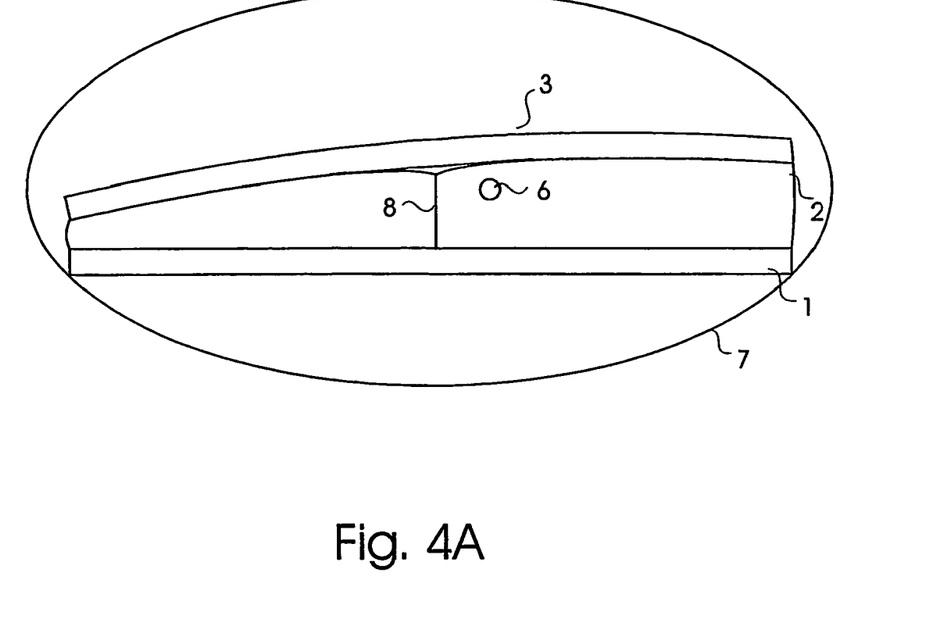
FIG. 4A represents an alternative embodiment of the inventive pillow system in side view.
Figure 4B:
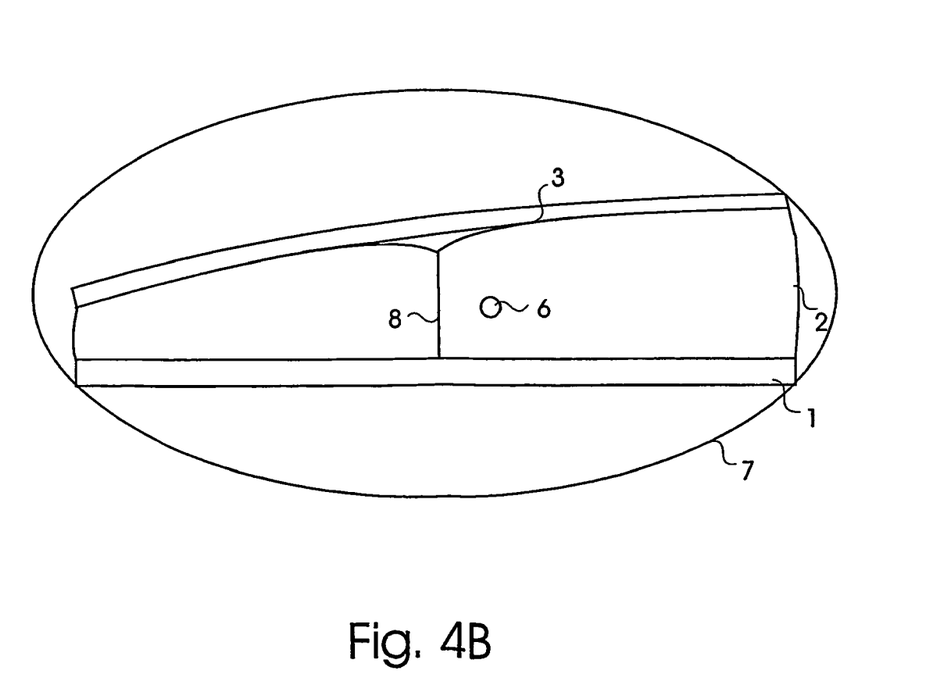
FIG. 4B represents this embodiment of the pillow system, further inflated.

FIG. 4A represents an alternative embodiment of the inventive pillow system in side view, where on a basis element 1 made of a flat layer of a relatively high density foam an inflatable pillow 2 is placed which has a wedge-shaped cross section, while on top of inflatable pillow 2 a layer 3 made of a relatively low density foam is placed. FIG. 4B represents this embodiment of the pillow system, further inflated, from which it can be seen that when the pillow is inflated, layer 3 will rise but also the angle will increase, which means that a continuous range of supporting positions for the head of a user can be realised. In order to prevent the top side of inflatable pillow from becoming spherically shaped, inflatable pillow 2 is provided with a number of partitions 8, which will keep the shape of inflatable pillow 2 at least substantially constant, a technique that is well known in the art. Preferably, a cover 7 is pulled round the pillow system which is made of an elastic fabric, for example of so called stretch textile, which is shown in the figure in a strained situation but which will under operational conditions tightly enclose the other components of the pillow system and prevent in this way the components from moving with respect to one another.

Figure 5A:
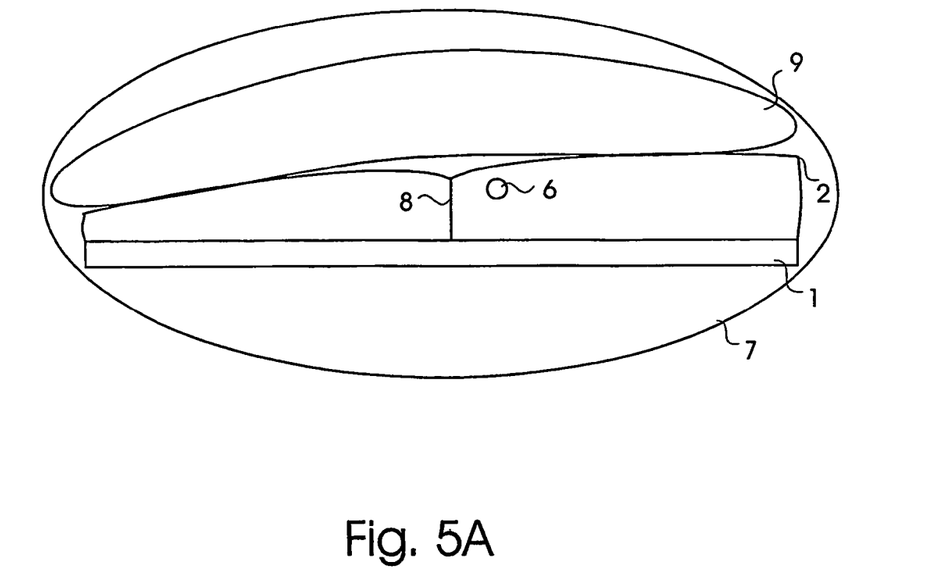
FIG. 5A represents an alternative embodiment of the inventive pillow system that can be used together with a traditional pillow.
Figure 5B:
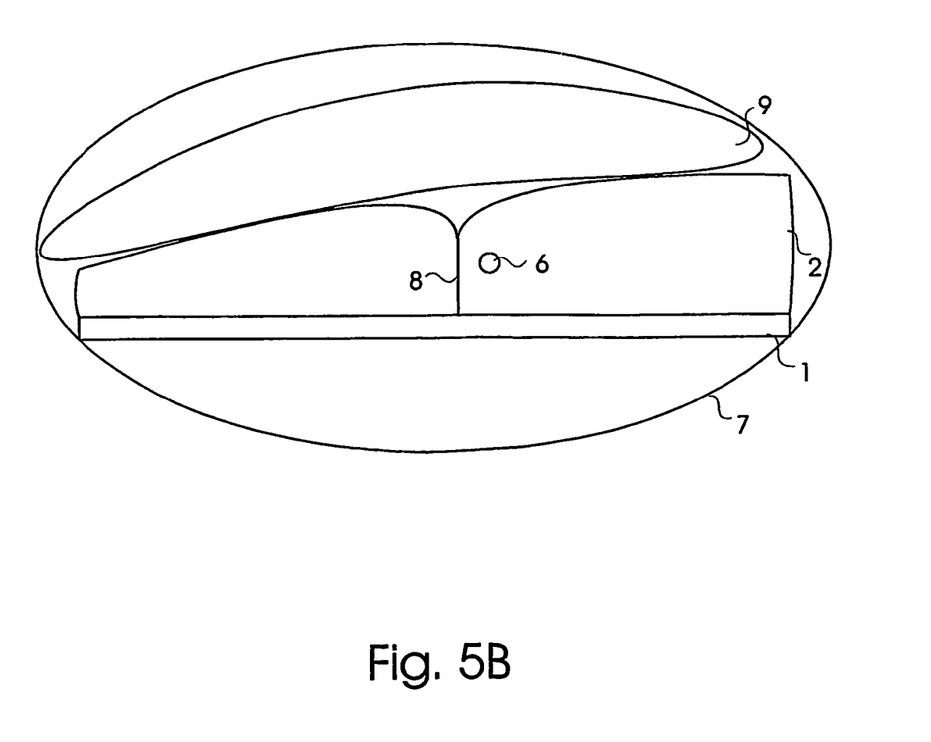
FIG. 5B represents this embodiment with a further inflated pillow system.

FIG. 5A represents an alternative embodiment of the inventive pillow system, where on a basis element 1 made of a flat layer of a relatively high density foam an inflatable pillow 2 is placed which has a wedge-shaped cross section, while on top of inflatable pillow 2 and within cover 7 a traditional pillow can be placed. FIG. 5B represents this embodiment of the pillow system, further inflated, from which it can be seen that pillow 9 rises but also that the angle increases, which means that a continuous range of supporting positions for the head of a user can be realised. In order to prevent the top side of inflatable pillow 2 from becoming spherically shaped, it is provided with a number of partitions 8, which will keep the shape of inflatable pillow 3 at least substantially constant, a technique that is well known in the art. Preferably, a cover 7 is pulled round the pillow system which is made of an elastic fabric, for example of so called stretch textile, which is shown in the figure in a strained situation but which will under operational conditions tightly enclose the other components of the pillow system and prevent in this way the components from moving with respect to one another.

Figure 6A:
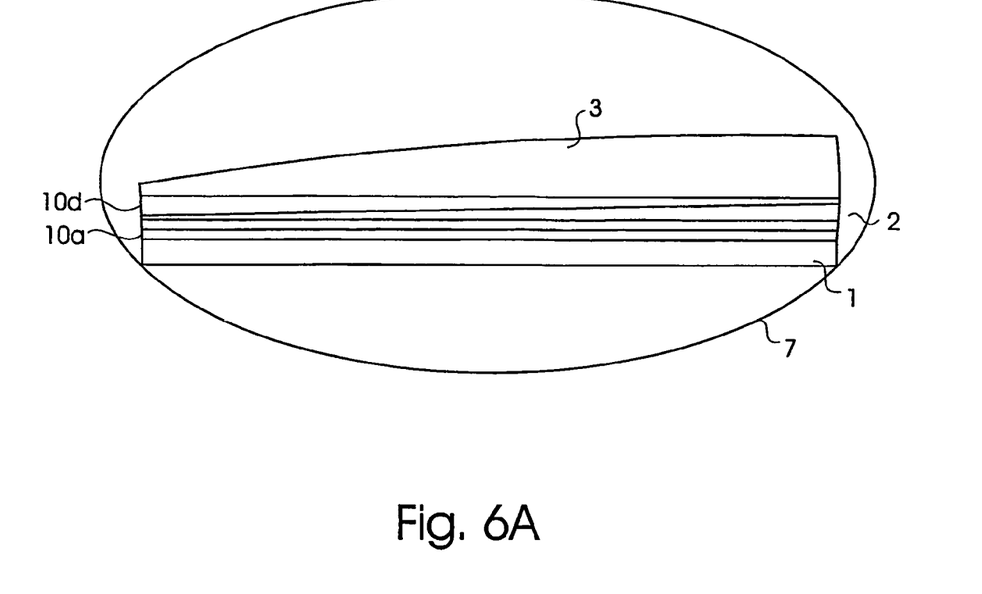
FIG. 6A represents an alternative embodiment of the inventive pillow system with foam layers in a first possible position.
Figure 6B:
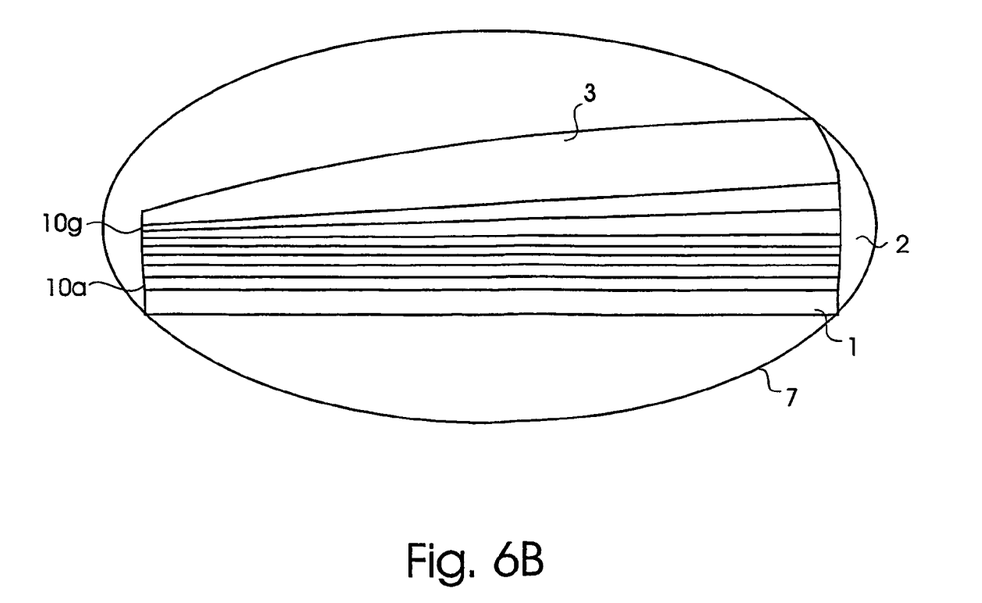
FIG. 6B represents this embodiment of the pillow system in a second possible position.

FIG. 6A represents an alternative embodiment of the inventive pillow system with foam layers in a first possible position, where on a basis element 1 made of a flat layer of a relatively high density foam an adjustable pillow 2 is placed which consists in this embodiment of four foam layers 10*a*, . . . , 10*d* which may be removed or added by a user in a simple manner in order to obtain an optimal thickness. Layer 10*c* and layer 10*d* here have a wedge-shaped cross section, but they are arranged here in such a way that they do not alter the angle of the pillow system. On pillow 2, a top layer 3 made of a relatively low density foam is placed. If desired, the own, familiar pillow of a user can be placed on top of top layer 3 or it may replace top layer 3, in which case cover 7 keeps the components in place. FIG. 6B represents this embodiment of the pillow system in a second possible position, where pillow 2 consists of seven layers 10*a*, . . . , 10*g* and where two wedge-shaped layers 10*f*, 10*g* are arranged in such a way that they increase the angle respectively the shape of the pillow system.

The invention claimed is:

1. Pillow system for preventing snoring, comprising:
   at least a basis element made of foam rubber, polyurethane foam, polyether foam or a comparable foam product, the basis element being at least substantially flat;
   an adjustable pillow fitted onto the basis element, the adjustable pillow having a shape that slopes at an angle from a first thickness at a front end of the pillow to a second thickness at a back end of the pillow so as to be in a longitudinal cross section at least substantially wedge-shaped; and
   a cover for enclosing the basis element and the adjustable pillow.

2. Pillow system according to claim 1, characterized in that the adjustable pillow is an inflatable pillow.

3. Pillow system according to claim 2, characterized in that the basis element is provided with a depression, under operational condition transverse positioned to a user, which at least partly encloses the inflatable pillow.

4. Pillow system according to claim 3, characterized in that on one side the basis element is provided with a flap made of foam rubber, polyurethane foam, polyether foam or a comparable foam product and that under operational conditions the flap is positioned on top of the inflatable pillow.

5. Pillow system according to claim 3, characterized in that the basis element is made of a relatively high density foam rubber, polyurethane foam, polyether foam or a comparable foam product and the flap of relatively low density foam rubber, polyurethane foam, polyether foam or a comparable foam product.

6. Pillow system according to claim 1, characterized in that the adjustable pillow comprises a number of layers made of a relatively high-density foam rubber, polyurethane foam, polyether foam or a comparable foam product.

7. Pillow system according to claim 6, characterized in that at least one layer is in a longitudinal cross section at least substantially wedge-shaped.

8. Pillow system according to claim 1, characterized in that the top side of the pillow system is provided with a layer made of a relatively low density foam rubber, polyurethane foam, polyether foam or a comparable foam product.

9. Pillow system according to claim 1, characterized in that the cover is made of an elastic material and can be placed around the other constituent parts of the pillow system.

10. Pillow system according to claim 1, wherein the adjustable pillow is capable of being adjusted to vary the slope angle from the front end of the pillow to the back end of the pillow.

11. Pillow system according to claim 10, wherein adjustment of the adjustable pillow to vary the slope angle from the front end of the pillow to the back end of the pillow is achieved by inflation of the adjustable pillow.

12. Pillow system according to claim 10, wherein the adjustable pillow comprises a number of layers made of a relatively high-density foam rubber, polyurethane foam, polyether foam or a comparable foam product, and adjustment of the adjustable pillow to vary the slope angle from the front end of the pillow to the back end of the pillow is achieved by changing the number of layers of the adjustable pillow.

13. Pillow system according to claim 12, wherein at least one of the number of layers is in a longitudinal cross-section at least substantially wedge-shaped.

* * * * *